(12) United States Patent
Davison et al.

(10) Patent No.: US 7,691,101 B2
(45) Date of Patent: Apr. 6, 2010

(54) ELECTROSURGICAL METHOD AND SYSTEM FOR TREATING FOOT ULCER

(75) Inventors: Terry S. Davison, Redwood City, CA (US); Brian Warne, Los Gatos, CA (US)

(73) Assignee: ArthroCare Corporation, Austin, TX (US)

( * ) Notice: Subject to any disclaimer, the term of this patent is extended or adjusted under 35 U.S.C. 154(b) by 783 days.

(21) Appl. No.: 11/327,089

(22) Filed: Jan. 6, 2006

(65) Prior Publication Data

US 2007/0213700 A1    Sep. 13, 2007

(51) Int. Cl.
    *A61B 18/18* (2006.01)
(52) U.S. Cl. .............................. 606/41; 606/45; 606/49; 606/50
(58) Field of Classification Search ................ 128/898; 606/41, 45, 49–50
    See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1936 | Wappler | 125/303 |
| 3,633,425 A | 1/1972 | Sanford | 73/356 |
| 3,707,149 A | 12/1972 | Hao et al. | 128/303.14 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |

(Continued)

FOREIGN PATENT DOCUMENTS

DE        3930451 A1    3/1991

(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.

(Continued)

*Primary Examiner*—Michael Peffley
*Assistant Examiner*—Vincent Sica
(74) *Attorney, Agent, or Firm*—Matthew Scheele; Brian E. Szymczak

(57) ABSTRACT

An electrosurgical method for treating foot ulcer, including diabetic foot ulcer, comprising: positioning an active electrode in close proximity to the ulcer, the active electrode being disposed on a distal end of an electrosurgical shaft; applying a high-frequency voltage potential difference across the active electrode and a return electrode in the presence of an electrically conductive fluid, the voltage potential being sufficient to generate plasma at the active electrode; and stimulating the ulcer with the active electrode to increase blood flow, remove unhealthy tissue and induce the body's natural healing response.

29 Claims, 4 Drawing Sheets

U.S. PATENT DOCUMENTS

| | | | |
|---|---|---|---|
| 4,202,337 A | 5/1980 | Hren et al. ................. 128/303 |
| 4,228,800 A | 10/1980 | Degler, Jr. et al. ........... 128/303 |
| 4,232,676 A | 11/1980 | Herczog ..................... 128/303 |
| 4,240,441 A | 12/1980 | Khalil ........................ 600/505 |
| 4,248,231 A | 2/1981 | Herczog et al. ............. 128/303 |
| 4,301,801 A | 11/1981 | Schneiderman ............. 606/38 |
| 4,326,529 A | 4/1982 | Doss et al. .................. 128/303 |
| 4,346,715 A | 8/1982 | Gammell ..................... 607/99 |
| 4,381,007 A | 4/1983 | Doss ........................... 128/303 |
| 4,418,692 A | 12/1983 | Guay .......................... 606/42 |
| 4,474,179 A | 10/1984 | Koch ........................... 606/40 |
| 4,476,862 A | 10/1984 | Pao ............................. 128/303 |
| 4,520,818 A | 6/1985 | Mickiewicz ................. 606/40 |
| 4,532,924 A | 8/1985 | Auth et al. ................... 128/303 |
| 4,548,207 A | 10/1985 | Reimels ....................... 128/303 |
| 4,567,890 A | 2/1986 | Ohta et al. ................... 128/303 |
| 4,572,206 A | 2/1986 | Geddes et al. ............... 600/505 |
| 4,580,557 A | 4/1986 | Hertzmann .................. 606/12 |
| 4,587,975 A | 5/1986 | Salo et al. .................... 600/506 |
| 4,590,934 A | 5/1986 | Malis et al. .................. 128/303 |
| 4,593,691 A | 6/1986 | Lindstrom et al. ........... 128/303 |
| 4,658,817 A | 4/1987 | Hardy ......................... 606/14 |
| 4,660,571 A | 4/1987 | Hess et al. ................... 128/784 |
| 4,674,499 A | 6/1987 | Pao ............................. 128/303 |
| 4,682,596 A | 7/1987 | Bales et al. .................. 128/303 |
| 4,706,667 A | 11/1987 | Roos ........................... 128/303 |
| 4,709,698 A | 12/1987 | Johnston et al. ............. 606/41 |
| 4,727,874 A | 3/1988 | Bowers et al. ............... 128/303 |
| 4,765,331 A | 8/1988 | Petruzzi et al. .............. 128/303 |
| 4,785,823 A | 11/1988 | Eggers et al. ................ 128/692 |
| 4,805,616 A | 2/1989 | Pao ............................. 128/303 |
| 4,823,791 A | 4/1989 | D'Amelio et al. ............ 123/303 |
| 4,832,048 A | 5/1989 | Cohen ......................... 128/786 |
| 4,860,752 A | 8/1989 | Turner ......................... 607/152 |
| 4,898,169 A | 2/1990 | Norman et al. ............... 606/42 |
| 4,907,589 A | 3/1990 | Cosman ....................... 606/34 |
| 4,920,978 A | 5/1990 | Colvin ......................... 128/784 |
| 4,931,047 A | 6/1990 | Broadwin et al. ............ 604/22 |
| 4,936,281 A | 6/1990 | Stasz ........................... 128/660 |
| 4,936,301 A | 6/1990 | Rexroth et al. ............... 606/45 |
| 4,943,290 A | 7/1990 | Rexroth et al. ............... 606/45 |
| 4,955,377 A | 9/1990 | Lennox et al. ................ 607/105 |
| 4,966,597 A | 10/1990 | Cosman ....................... 606/50 |
| 4,967,765 A | 11/1990 | Turner et al. ................. 128/785 |
| 4,976,711 A | 12/1990 | Parins et al. .................. 606/48 |
| 4,979,948 A | 12/1990 | Geddes et al. ............... 606/33 |
| 4,998,933 A | 3/1991 | Eggers et al. ................ 606/41 |
| 5,007,908 A | 4/1991 | Rydell ......................... 606/47 |
| 5,009,656 A | 4/1991 | Reimels ....................... 606/48 |
| 5,035,696 A | 7/1991 | Rydell ......................... 606/47 |
| 5,047,026 A | 9/1991 | Rydell ......................... 606/48 |
| 5,047,027 A | 9/1991 | Rydell ......................... 606/48 |
| 5,057,105 A | 10/1991 | Malone et al. ................ 606/28 |
| 5,057,106 A | 10/1991 | Kasevich et al. ............. 606/33 |
| 5,057,743 A | 10/1991 | Krasko et al. ................ 313/639 |
| 5,078,717 A | 1/1992 | Parins et al. .................. 606/48 |
| 5,080,660 A | 1/1992 | Buelna ......................... 606/45 |
| 5,083,565 A | 1/1992 | Parins et al. .................. 600/374 |
| 5,084,044 A | 1/1992 | Quint .......................... 606/27 |
| 5,085,659 A | 2/1992 | Rydell ......................... 606/47 |
| 5,088,997 A | 2/1992 | Delahuerga et al. .......... 606/42 |
| 5,092,339 A | 3/1992 | Geddes et al. ............... 606/505 |
| 5,098,431 A | 3/1992 | Rydell ......................... 606/48 |
| 5,099,840 A | 3/1992 | Goble .......................... 128/422 |
| 5,102,410 A | 4/1992 | Dressel ........................ 606/15 |
| 5,108,391 A | 4/1992 | Flachenecker et al. ....... 606/38 |
| RE33,925 E | 5/1992 | Bales et al. .................. 606/48 |
| 5,112,330 A | 5/1992 | Nishigaki et al. ............ 606/46 |
| 5,122,138 A | 6/1992 | Manwaring .................. 606/46 |
| 5,125,928 A | 6/1992 | Parins et al. .................. 606/48 |
| 5,156,151 A | 10/1992 | Imran .......................... 600/375 |
| 5,167,659 A | 12/1992 | Ohtomo et al. ............... 606/40 |
| 5,171,311 A | 12/1992 | Rydell et al. ................. 606/48 |
| 5,174,304 A | 12/1992 | Latina et al. ................. 607/141 |
| 5,178,620 A | 1/1993 | Eggers et al. ................ 606/41 |
| 5,183,338 A | 2/1993 | Wickersheim et al. ....... 374/131 |
| 5,190,517 A | 3/1993 | Zieve et al. .................. 604/22 |
| 5,192,280 A | 3/1993 | Parins .......................... 606/48 |
| 5,195,959 A | 3/1993 | Smith .......................... 604/34 |
| 5,197,466 A | 3/1993 | Marchosky et al. .......... 128/399 |
| 5,197,963 A | 3/1993 | Parins .......................... 606/46 |
| 5,207,675 A | 5/1993 | Canady ....................... 606/40 |
| 5,217,457 A | 6/1993 | Delahuerga et al. .......... 606/42 |
| 5,217,459 A | 6/1993 | Kamerling ................... 606/48 |
| 5,249,585 A | 10/1993 | Turner et al. ................. 607/99 |
| 5,255,980 A | 10/1993 | Thomas et al. ............... 374/161 |
| 5,261,410 A | 11/1993 | Alfano et al. ................ 600/475 |
| 5,267,994 A | 12/1993 | Gentelia et al. .............. 606/15 |
| 5,267,997 A | 12/1993 | Farin et al. .................. 606/38 |
| 5,273,524 A | 12/1993 | Fox et al. ..................... 604/21 |
| 5,277,201 A | 1/1994 | Stern ........................... 607/98 |
| 5,281,216 A | 1/1994 | Klicek ......................... 606/42 |
| 5,281,218 A | 1/1994 | Imran .......................... 606/41 |
| 5,290,282 A | 3/1994 | Casscells ..................... 606/29 |
| 5,300,069 A | 4/1994 | Hunsberger et al. .......... 606/37 |
| 5,306,238 A | 4/1994 | Fleenor ........................ 606/42 |
| 5,312,400 A | 5/1994 | Bales et al. .................. 606/41 |
| 5,314,406 A | 5/1994 | Arias et al. .................. 604/21 |
| 5,318,563 A | 6/1994 | Malis et al. .................. 606/38 |
| 5,324,254 A | 6/1994 | Phillips ....................... 604/21 |
| 5,330,470 A | 7/1994 | Hagen ......................... 606/42 |
| 5,334,140 A | 8/1994 | Philips ........................ 604/35 |
| 5,334,183 A | 8/1994 | Wuchinich ................... 606/46 |
| 5,334,193 A | 8/1994 | Nardella ...................... 606/41 |
| 5,336,220 A | 8/1994 | Ryan et al. ................... 604/22 |
| 5,336,443 A | 8/1994 | Odashima .................... 252/511 |
| 5,342,357 A | 8/1994 | Nardella ...................... 606/40 |
| 5,348,554 A | 9/1994 | Imran et al. .................. 606/41 |
| 5,363,324 A | 11/1994 | Hashimoto et al. .......... 365/156 |
| 5,366,443 A | 11/1994 | Eggers et al. ................ 604/114 |
| 5,370,675 A | 12/1994 | Edwards et al. ............. 607/101 |
| 5,374,261 A | 12/1994 | Yoon .......................... 604/385.01 |
| 5,375,588 A | 12/1994 | Yoon .......................... 128/4 |
| 5,380,277 A | 1/1995 | Phillips ....................... 604/33 |
| 5,380,316 A | 1/1995 | Aita ............................ 606/7 |
| 5,383,876 A | 1/1995 | Nardella ...................... 606/49 |
| 5,383,917 A | 1/1995 | Desai et al. .................. 607/702 |
| 5,389,096 A | 2/1995 | Aita ............................ 606/15 |
| 5,395,312 A | 3/1995 | Desai .......................... 604/22 |
| 5,400,267 A | 3/1995 | Denen et al. ................. 702/59 |
| 5,401,272 A | 3/1995 | Perkins ....................... 606/15 |
| 5,403,311 A | 4/1995 | Abele et al. ................. 606/49 |
| 5,417,687 A | 5/1995 | Nardella et al. ............. 606/32 |
| 5,419,767 A | 5/1995 | Eggers et al. ................ 604/114 |
| 5,423,810 A | 6/1995 | Goble et al. ................. 606/40 |
| 5,423,882 A | 6/1995 | Jackman et al. ............. 607/122 |
| 5,436,566 A | 7/1995 | Thompson et al. .......... 324/713 |
| 5,437,662 A | 8/1995 | Nardella ...................... 606/40 |
| 5,438,302 A | 8/1995 | Goble .......................... 331/167 |
| 5,441,499 A | 8/1995 | Fritzsch ....................... 606/45 |
| 5,451,224 A | 9/1995 | Goble et al. ................. 606/48 |
| 5,454,809 A | 10/1995 | Janssen ....................... 606/41 |
| 5,458,596 A | 10/1995 | Lax et al. .................... 606/31 |
| 5,458,597 A | 10/1995 | Edwards et al. ............. 606/41 |
| 5,472,443 A | 12/1995 | Cordis et al. ................ 606/48 |
| 5,486,161 A | 1/1996 | Lax et al. .................... 604/22 |
| 5,496,312 A | 3/1996 | Klicek ........................ 606/34 |
| 5,496,314 A | 3/1996 | Eggers ........................ 606/41 |
| 5,496,317 A | 3/1996 | Goble et al. ................. 606/48 |
| 5,505,730 A | 4/1996 | Edwards et al. ............. 606/41 |
| 5,514,130 A | 5/1996 | Baker .......................... 606/41 |
| 5,542,915 A | 8/1996 | Edwards et al. ............. 604/22 |
| 5,549,598 A | 8/1996 | O'Donnell, Jr. .............. 606/6 |
| 5,554,152 A | 9/1996 | Aita ............................ 606/7 |

| | | | | | | | |
|---|---|---|---|---|---|---|---|
| 5,556,397 A | 9/1996 | Long et al. ............. 606/48 | | 6,149,620 A | 11/2000 | Baker et al. ............. 604/22 |
| 5,562,703 A | 10/1996 | Desai ................. 606/210 | | 6,159,194 A | 12/2000 | Eggers et al. ........... 604/500 |
| 5,569,242 A | 10/1996 | Lax et al. ............. 606/42 | | 6,159,208 A | 12/2000 | Hovda et al. ............. 606/41 |
| 5,571,100 A | 11/1996 | Goble et al. ............. 606/41 | | 6,162,217 A | 12/2000 | Kannenberg et al. ......... 606/34 |
| 5,584,872 A | 12/1996 | LaFontaine et al. ......... 607/117 | | 6,168,593 B1 | 1/2001 | Sharkey et al. ............. 606/34 |
| 5,588,960 A | 12/1996 | Edwards et al. ............. 604/20 | | 6,174,309 B1 | 1/2001 | Wrublewski et al. ......... 606/45 |
| 5,599,350 A | 2/1997 | Schulze et al. ............. 606/51 | | 6,179,824 B1 | 1/2001 | Eggers et al. ........... 604/500 |
| 5,609,151 A | 3/1997 | Mulier et al. ............. 128/642 | | 6,179,836 B1 | 1/2001 | Eggers et al. ............. 606/45 |
| 5,633,578 A | 5/1997 | Eggers et al. ............. 323/301 | | 6,183,469 B1 | 2/2001 | Thapliyal et al. ........... 606/41 |
| 5,634,921 A | 6/1997 | Hood et al. ............. 606/1 | | 6,190,381 B1 | 2/2001 | Olsen et al. ............. 606/32 |
| 5,647,869 A | 7/1997 | Goble et al. ............. 606/37 | | 6,197,021 B1 | 3/2001 | Panescu et al. ............. 606/31 |
| 5,658,278 A | 8/1997 | Imran et al. ............. 606/41 | | 6,203,542 B1 | 3/2001 | Ellsberry et al. ........... 606/41 |
| 5,660,567 A | 8/1997 | Nierlich et al. ......... 439/620.21 | | 6,210,402 B1 | 4/2001 | Olsen et al. ............. 606/32 |
| 5,662,680 A | 9/1997 | Desai ................. 606/210 | | 6,210,405 B1 | 4/2001 | Goble et al. ............. 606/41 |
| 5,676,693 A | 10/1997 | LaFontaine et al. ......... 607/116 | | 6,224,592 B1 | 5/2001 | Eggers et al. ............. 606/32 |
| 5,681,282 A | 10/1997 | Eggers et al. ............. 604/114 | | 6,228,078 B1 | 5/2001 | Eggers ................. 606/32 |
| 5,683,366 A | 11/1997 | Eggers et al. ............. 604/114 | | 6,228,081 B1 | 5/2001 | Goble ................. 606/34 |
| 5,697,281 A | 12/1997 | Eggers et al. ............. 604/114 | | 6,234,178 B1 | 5/2001 | Goble ................. 606/32 |
| 5,697,536 A | 12/1997 | Eggers et al. ............. 604/114 | | 6,235,020 B1 | 5/2001 | Cheng et al. ............. 606/34 |
| 5,697,882 A | 12/1997 | Eggers et al. ............. 604/114 | | 6,237,604 B1 | 5/2001 | Burnside et al. ............. 128/897 |
| 5,697,909 A | 12/1997 | Eggers et al. ............. 604/114 | | 6,238,391 B1 | 5/2001 | Olsen et al. ............. 606/41 |
| 5,700,262 A | 12/1997 | Acosta et al. ............. 606/48 | | 6,254,600 B1 | 7/2001 | Willink et al. ............. 606/41 |
| 5,715,817 A | 2/1998 | Steven-Wright et al. .... 600/373 | | 6,261,286 B1 | 7/2001 | Goble et al. ............. 606/34 |
| 5,722,975 A | 3/1998 | Edwards et al. ............. 606/41 | | 6,261,311 B1 | 7/2001 | Sharkey et al. ............. 607/96 |
| 5,725,524 A | 3/1998 | Mulier et al. ............. 606/41 | | 6,264,652 B1 | 7/2001 | Eggers et al. ............. 606/41 |
| 5,749,869 A | 5/1998 | Lindenmeier et al. ......... 606/34 | | 6,270,460 B1 | 8/2001 | McCartan et al. ........... 600/459 |
| 5,755,753 A | 5/1998 | Knowlton ................. 607/98 | | 6,277,112 B1 | 8/2001 | Underwood et al. ......... 606/32 |
| 5,766,153 A | 6/1998 | Eggers et al. ............. 604/114 | | 6,280,441 B1 | 8/2001 | Ryan ................. 606/45 |
| 5,769,847 A | 6/1998 | Panescu et al. ............. 606/42 | | 6,283,961 B1 | 9/2001 | Underwood et al. ......... 604/41 |
| 5,785,705 A | 7/1998 | Baker ................. 606/32 | | 6,293,942 B1 | 9/2001 | Goble et al. ............. 606/38 |
| 5,786,578 A | 7/1998 | Christy et al. ............. 219/720 | | 6,296,636 B1 | 10/2001 | Cheng et al. ............. 606/32 |
| 5,800,429 A | 9/1998 | Edwards ................. 606/41 | | 6,296,638 B1 | 10/2001 | Davison et al. ............. 606/41 |
| 5,807,395 A | 9/1998 | Mulier et al. ............. 606/41 | | 6,306,134 B1 | 10/2001 | Goble et al. ............. 606/42 |
| 5,810,764 A | 9/1998 | Eggers et al. ............. 604/23 | | 6,308,089 B1 | 10/2001 | von der Rur et al. ......... 600/338 |
| 5,810,802 A | 9/1998 | Panescu et al. ............. 606/31 | | 6,309,387 B1 | 10/2001 | Eggers et al. ............. 606/41 |
| 5,810,809 A | 9/1998 | Rydell ................. 606/49 | | 6,312,408 B1 | 11/2001 | Eggers et al. ............. 604/114 |
| 5,836,875 A | 11/1998 | Webster, Jr. ............. 600/374 | | 6,322,549 B1 | 11/2001 | Eggers et al. ............. 604/500 |
| 5,843,019 A | 12/1998 | Eggers et al. ............. 604/22 | | 6,345,104 B1 | 2/2002 | Rhoads et al. ............. 606/34 |
| 5,860,951 A | 1/1999 | Eggers ................. 604/510 | | 6,355,032 B1 | 3/2002 | Hovda et al. ............. 606/32 |
| 5,860,974 A | 1/1999 | Abele ................. 606/41 | | 6,363,937 B1 | 4/2002 | Hovda et al. ............. 128/898 |
| 5,860,975 A | 1/1999 | Goble et al. ............. 606/45 | | 6,364,877 B1 | 4/2002 | Goble et al. ............. 606/34 |
| 5,871,469 A | 2/1999 | Eggers et al. ............. 604/114 | | 6,379,351 B1 | 4/2002 | Thapliyal et al. ........... 606/41 |
| 5,873,855 A | 2/1999 | Eggers et al. ............. 604/114 | | 6,391,025 B1 | 5/2002 | Weinstein et al. ........... 606/41 |
| 5,873,877 A | 2/1999 | McGaffigan ............. 606/41 | | 6,409,722 B1 | 6/2002 | Hoey et al. ............. 606/34 |
| 5,885,277 A | 3/1999 | Korth ................. 606/35 | | 6,416,507 B1 | 7/2002 | Eggers et al. ............. 606/32 |
| 5,888,198 A | 3/1999 | Eggers et al. ............. 604/114 | | 6,416,508 B1 | 7/2002 | Eggers et al. ............. 606/32 |
| 5,891,095 A | 4/1999 | Eggers et al. ............. 604/114 | | 6,416,509 B1 | 7/2002 | Goble et al. ............. 606/37 |
| 5,891,134 A | 4/1999 | Goble et al. ............. 606/27 | | 6,432,103 B1 | 8/2002 | Ellsberry et al. ........... 606/41 |
| 5,897,553 A | 4/1999 | Mulier ................. 606/41 | | 6,440,129 B1 | 8/2002 | Simpson ................. 606/42 |
| 5,902,272 A | 5/1999 | Eggers et al. ............. 604/114 | | 6,468,274 B1 | 10/2002 | Alleyne et al. ............. 606/32 |
| 5,944,715 A | 8/1999 | Goble et al. ............. 606/41 | | 6,468,275 B1 | 10/2002 | Wampler et al. ............. 606/48 |
| 5,954,716 A | 9/1999 | Sharkey et al. ............. 606/32 | | 6,482,201 B1 | 11/2002 | Olsen et al. ............. 606/41 |
| 5,964,786 A | 10/1999 | Ochs et al. ............. 607/5 | | 6,517,498 B1 | 2/2003 | Burbank et al. ............. 600/564 |
| 6,004,319 A | 12/1999 | Goble et al. ............. 606/48 | | 6,530,922 B2 | 3/2003 | Cosman ................. 606/34 |
| 6,013,076 A | 1/2000 | Goble et al. ............. 606/41 | | 6,558,382 B2 | 5/2003 | Jahns et al. ............. 606/41 |
| 6,015,406 A | 1/2000 | Goble et al. ............. 606/41 | | 6,578,579 B2 | 6/2003 | Burnside ................. 128/897 |
| 6,024,733 A | 2/2000 | Eggers et al. ............. 604/500 | | 6,589,237 B2 | 7/2003 | Woloszko et al. ........... 606/41 |
| 6,027,501 A | 2/2000 | Goble et al. ............. 606/41 | | 6,602,248 B1 | 8/2003 | Sharps et al. ............. 606/32 |
| 6,039,734 A | 3/2000 | Goble et al. ............. 606/41 | | 6,620,156 B1 | 9/2003 | Garito et al. ............. 606/50 |
| 6,047,700 A | 4/2000 | Eggers et al. ............. 128/898 | | 6,632,193 B1 | 10/2003 | Davison et al. ............. 604/22 |
| 6,056,746 A | 5/2000 | Goble et al. ............. 606/48 | | 6,632,220 B1 | 10/2003 | Eggers et al. ............. 606/41 |
| 6,063,079 A | 5/2000 | Hovda et al. ............. 606/41 | | 6,749,604 B1 | 6/2004 | Eggers et al. ............. 606/41 |
| 6,066,134 A | 5/2000 | Eggers et al. ............. 606/32 | | 6,749,608 B2 | 6/2004 | Garito et al. ............. 606/45 |
| 6,068,628 A | 5/2000 | Fanton et al. ............. 606/41 | | 6,770,071 B2 | 8/2004 | Woloszko et al. ........... 606/41 |
| 6,074,386 A | 6/2000 | Goble et al. ............. 606/41 | | 6,780,178 B2 | 8/2004 | Palanker et al. ............. 600/41 |
| 6,090,106 A | 7/2000 | Goble et al. ............. 606/41 | | 6,780,180 B1 | 8/2004 | Goble et al. ............. 606/41 |
| 6,093,186 A | 7/2000 | Goble et al. ............. 606/34 | | 6,802,842 B2 | 10/2004 | Ellman et al. ............. 606/45 |
| 6,102,046 A | 8/2000 | Weinstein et al. ........... 128/898 | | 6,805,130 B2 | 10/2004 | Tasto et al. ............. 606/41 |
| 6,105,581 A | 8/2000 | Eggers et al. ............. 128/898 | | 6,837,887 B2 | 1/2005 | Woloszko et al. ........... 606/41 |
| 6,109,268 A | 8/2000 | Thapliyal et al. ........... 128/898 | | 6,837,888 B2 | 1/2005 | Ciarrocca et al. ........... 606/41 |
| 6,117,109 A | 9/2000 | Eggers et al. ............. 604/114 | | 6,866,671 B2 | 3/2005 | Tierney et al. ............. 606/130 |
| 6,126,682 A | 10/2000 | Sharkey et al. ............. 607/96 | | 6,878,149 B2 | 4/2005 | Gatto ................. 606/46 |
| 6,142,992 A | 11/2000 | Cheng et al. ............. 606/34 | | 6,890,307 B2 | 5/2005 | Kokate et al. ............. 600/549 |

| Patent No. | Date | Inventor | Class |
|---|---|---|---|
| 6,892,086 B2 | 5/2005 | Russell | 600/372 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,855 B1 | 1/2006 | Hood | 451/6 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,276,063 B2 | 10/2007 | Davison et al. | 606/45 |
| 7,278,994 B2 | 10/2007 | Goble | 606/41 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 2002/0029036 A1 | 3/2002 | Goble et al. | 606/38 |
| 2002/0042612 A1 | 4/2002 | Hood et al. | 606/50 |
| 2002/0095151 A1 | 7/2002 | Dahla et al. | 606/41 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0130655 A1 | 7/2003 | Woloszko et al. | 606/45 |
| 2003/0130707 A1* | 7/2003 | Gan et al. | 607/50 |
| 2003/0158545 A1 | 8/2003 | Hovda et al. | 606/32 |
| 2003/0171743 A1 | 9/2003 | Tasto et al. | 606/32 |
| 2003/0181903 A1 | 9/2003 | Hood et al. | 606/49 |
| 2003/0208194 A1 | 11/2003 | Hovda et al. | 606/41 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0024399 A1 | 2/2004 | Sharps et al. | 606/32 |
| 2004/0030330 A1* | 2/2004 | Brassell et al. | 606/41 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0186470 A1* | 9/2004 | Goble et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Ricart et al. | 606/32 |
| 2006/0095031 A1 | 5/2006 | Ormsby | 606/34 |
| 2006/0129145 A1 | 6/2006 | Woloszko et al. | 606/41 |
| 2006/0178670 A1 | 8/2006 | Woloszko et al. | 606/48 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Sanders et al. | 606/32 |
| 2007/0106288 A1 | 5/2007 | Woloszko et al. | 606/41 |
| 2007/0112346 A1 | 5/2007 | Underwood et al. | 606/41 |
| 2007/0112348 A1 | 5/2007 | Eggers et al. | 606/41 |
| 2007/0129715 A1 | 6/2007 | Eggers et al. | 606/32 |
| 2007/0149966 A1 | 6/2007 | Dahla et al. | 606/41 |
| 2007/0161981 A1 | 7/2007 | Sanders et al. | 606/41 |
| 2007/0179497 A1 | 8/2007 | Eggers et al. | 606/41 |
| 2007/0208334 A1 | 9/2007 | Woloszko et al. | 606/41 |
| 2007/0208335 A1 | 9/2007 | Woloszko et al. | 606/41 |
| 2007/0213700 A1 | 9/2007 | Davison et al. | 606/32 |
| 2007/0282323 A1 | 12/2007 | Woloszko et al. | 606/41 |

FOREIGN PATENT DOCUMENTS

| | | |
|---|---|---|
| EP | 0703461 A2 | 3/1996 |
| EP | 0740926 A2 | 11/1996 |
| EP | 0 754 437 | 1/1997 |
| EP | 0 694 290 | 11/2000 |
| EP | 1334699 | 8/2003 |
| FR | 2313949 | 1/1977 |
| GB | 467502 | 6/1937 |
| GB | 2299216 | 9/1996 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/43971 | 11/1997 |
| WO | 97/48345 | 12/1997 |
| WO | 97/48346 | 12/1997 |

| | | |
|---|---|---|
| WO | 98/07468 | 2/1998 |
| WO | 98/26724 | 6/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 99/56648 | 11/1999 |
| WO | 00/00098 | 1/2000 |
| WO | 00/09053 | 2/2000 |
| WO | 01/24720 | 4/2001 |
| WO | 01/87154 | 5/2001 |
| WO | 02/36028 | 5/2002 |
| WO | 02/102255 | 12/2002 |
| WO | 03/024305 | 3/2003 |
| WO | 03/092477 | 11/2003 |
| WO | 2004/071278 | 8/2004 |
| WO | 2005/125287 | 12/2005 |
| WO | 2006/116252 | 11/2006 |
| WO | 2007/006000 | 1/2007 |
| WO | 2007/056729 | 5/2007 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
PCT International Search Report for PCT/US99/14685, 1 pg, mailed Oct. 21, 1999.
PCT Notification of International Preliminary Examination Report for PCT/US99/14685, 4 pgs, mailed Feb. 20, 2001.
PCT International Search Report for PCT/US98/22323, 1 pg, mailed Mar. 3, 1999.
PCT Notification of International Preliminary Examination Report for PCT/US98/22323, 5 pgs, mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, mailed Dec. 7, 1999.
PCT Notification of International Preliminary Examination Report for PCT/US99/18289, 4 pgs, mailed Jul. 7, 2000.
European Search Report for EP 99945039.8, 3 pgs, Oct. 1, 2001.
PCT International Search Report for PCT/US02/19261, 1 pg, mailed Sep. 18, 2002.
PCT International Preliminary Examination Report for PCT/US02/19261, 3 pgs, Mar. 25, 2003.
PCT International Seach Report for PCT/US02/29476, 1 pg, mailed May 24, 2004.
PCT International Search Report for PCT/US03/13686, 1 pg, mailed Nov. 25, 2003.
PCT International Search Report for PCT/US04/03614, 1 pg, mailed Sep. 14, 2004.
PCT Written Opinion of the International Searching Authority for PCT/US04/03614, 4 pgs, mailed Sep. 14, 2004.
EP Communication, European Examination Report for EP 98953859.0, 3 pgs, Jun. 14, 2004.
EP Communication, European Examination Report for EP 99945039.8, 5 pgs, May 10, 2004.
PCT Notification of International Search Report and Written Opinion for PCT/US06/26321, 8pgs, mailed Apr. 25, 2007.
PCT Notification of the International Search Report and Written Opinion for PCT/US06/60618, 7pgs, mailed Oct. 5, 2007.
Barry et al., "The Effect of Radiofrequency-generated Thermal Energy on the Mechanical and Histologic Characteristics of the Arterial Wall in Vivo: Implications of Radiofrequency Angioplasty" American Heart Journal vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.
Kramolowsky et al. "The Urological App of Electorsurgery" J. of Urology vol. 146, pp. 669-674, 1991.
Kramolowsky et al. "Use of 5F Biopolar Electrosurgical Probe in Endoscopic Urological Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.
Malis, L., "Electrosurgery, Technical Note," J. Neursurg., vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" Cerebrovascular Surgery, vol. 1, pp. 245-260, 1985.
Malis, L., "New Trends in Microsurgery and Applied Technology," Advanced Technology on Neurosurgery, pp. 1-16, 1988.
Malis, L., "The Value of Irrigation During Bipolar Coagulation" See ARTC 21602, 1 pg, Apr. 9, 1993.
Nardella, P.C., SPIE 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Biopolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, pp. 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, pp. 67-71, 1987.
Slager et al. "Vaporization of Atherosclerotice Plaques by Spark Erosion" JACC 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the 55th Gaseous Electronics Conference in Minneapolis, MN, 41 pgs, Oct. 14, 2002.

Soffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

Swain, C.P., et al., "Which Electrode, A Comparison for four endoscopic methods of electrocoagulation in experimental bleeding ulcers" *Gut* vol. 25, pp. 1424-1431, 1987.

Tucker, R. et al., "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs, 1991.

Valley Forge's New Products, Clinica, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 1990.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endroscopic electrodes, and tissue," Gastrointestinal Endoscopy, vol. 38, No. 2, pp. 118-122, 1992.

PCT Notification of the International Search Report and Written Opinion for PCT/US07/69856, 7pgs, mailed Jun. 5, 2008.

UK Search Report for GB0805062.7, 1 pg, Jul 16, 2008.

European Examination Report for EP 05024974, 4 pgs, Dec. 5, 2008.

European Search Report for EP 02773432, 3pgs, Dec. 19, 2008.

Rhyu, Kee-Won et al., "The short-term effects of electrosurgical ablation on proinflammatory meditor production by intervertebral disc cells in tissue culture", The Spine Journal 7, pp. 451-458, 2007.

O'Neill, Conor W. et al., "Percutaneous plasma decompression alters cytokine expression in injured porcine intervertebral discs", The Spine Journal 4, pp. 88-98, 2004.

Callaghan, Matthew J. et al., "Pulsed Electromagnetic Fields Accelerate Normal and Diabetic Wound Healing by Increasing Endogenous FGF-2 Release", Plastic and Reconstructive Surgery Journal, vol. 121, No. 1, Diabetic Wound Healing, <www.PRSJournal.com>, pp. 130-141, Jan. 2008.

"The 4th International Workshop on Microplasmas", Conference Center of NCKU Library, 19 pgs, Oct. 28-31, 2007.

Arniel et al., "Bipolar Radiofrequency-based Microtenotomy: Basic Science, Clinical Outcomes and mechanism of Action", Univ. of California, San Diego-Dept. of Orthopaedic Surg., San Diego Sports Med. and Orthopaedic Ctr, pp. 1-11, Mar. 29, 2007.

Balasubramanian et al., "Mechanism of Blood Coagulation by Non-Therman Atmospheric Pressure Dielectric Barrier Discharge Plasma", IEEE Transactions on Plasma Science, vol. 35, Issue 5, Part 2, pp. 1559-1566, Oct. 2007.

Fridman et al., "Applied Plasma Medicine", Plasma Process. Polym., Drexel Univ., pp. 1-56, 2007.

Fridman et al., "Bio-Medical Applications of Non-Thermal Atmospheric Pressure Plasma", 37th AIAA Plasmadynamics and Lasers Conference, 5 pgs, Jun. 5-8, 2006.

Fridman et al., "Blood Coagulation and Living Tissue Sterilization by Floating-electrode Dielectric Barrier Discharge in Air", Plasma Chem Plasma Process, Springer Science+Business Media, Inc., 18pgs, Feb. 2006.

Fridman et al., "Comparison of Direct and Indirect Effects of Non-Thermal Atomspheric-Pressure Plasma on Bacteria", Plasma Processes and Polymers, pp. 370-375, 2007.

Fridman et al., "Comparison of Sterilization by Floating Electrode Dielectric Barrier Discharge with Plasma Jet and Mechanisms of Observed Differences", Drexel University Ninth Annual Research Innovation Scholarship and Creativity (RISC) Day, Drexel University, 1 pg, Apr. 17, 2007.

Fridman et al., "Floating Electrode Dielectric Barrier Discharge Plasma in Air Promoting Apoptotic Behavior in Melanoma Skin Cancer Cell Lines", Plasma Chem Plasma Process, Springer Science+Business Media, LLC, 14 pgs, Jan. 2007.

Fridman et al., "Use of Non-Thermal Atmospheric Pressure Plasma Discharge for Coagulation and Sterilization of Surface Wounds", 17th International Symposium on Plasma Chemistry (ISPC-17), Toronto, Canada, 6 pgs, Aug. 7-12, 2005.

Funk et al., "Effects of Electromagnetic Fields on Cells: Physiological and Therapeutical Approaches and Molecular Mechanisms of Interaction", Cells Tissues Organs, vol. 182, pp. 59-78, 2006.

Hasan et al., "Sterilization using Atmospheric Pressure Non-Thermal Plasma", STAR Scholars Program, Pennoni Honors College, Drexel University, 1 pg, Aug. 15, 2007.

Kalghatgi et al., "Mechanism of Blood Coagulation by Nonthermal Atomspheric Pressure Dielectric Barrier Discharge Plasma", IEEE Transactions on Plasma Science, vol. 35, No. 5, pp. 1559-1566, Oct. 2007.

Lin et al., "Use of bipolar radiofrequency energy in delayed repair of acute supraspinatus tear in rats", J. Shoulder Elbow Surg, pp. 1-9, 2007.

Marine et al., "Wound Sterilization and Promoted Healing using Non-thermal Atmospheric Pressure Plasma", STAR Scholars Program, Pennoni Honors College, Drexel University, 1 pg, Apr. 2007.

Ochiai et al., "Nerve Regeneration After Radiofrequency Application", Am. J. Sports Med., pp. 1-5, 2007.

Robinson et al., "Biological and Medical Applications of Non-Thermal Atmospheric Pressure Plasma", STAR Scholars Program, Pennoni Honors College, Drexel University, 1 pg, Aug. 15, 2007.

Silver et al., "Thermal Microdebridement Does not Affect the Time Zero Biomechanical Properties of Human Patellar Tendons", Am. J. Sports Med., vol. 32, No. 8, pp. 1946-1952, 2004.

Takahashi et al., "Pain Relief Through and Antinociceptive Effect After Radiofrequency Application", Am. J. Sports Med., vol. 35, No. 5, pp. 805-810, 2007.

Tasto et al., "Microtenotomy Using a Radiofrequency Probe to Treat Lateral Epicondylitis", The Journal of Arthroscopic and Related Surgery, vol. 21, No. 7, pp. 851-860, Jul. 2005.

Tasto et al., "Radiofrequency Microtenotomy for Epicondylitis: Five-Year Follow-Up and Proposed Mechanism of Action (SS-65)", Presented at Spring AANA 2008, 1pg, 2008.

Tasto et al., "Radiofrequency-based Microtenotomy for Chronic Tendinosis of the Foot and Ankle", San Diego Sports Med. and Orthopaedic Ctr, Univ. of California San Diego—Dept. of Orthopaedics and Dept. of Biochem Research, Presented at the 2$^{nd}$ Triennial Scientific Meeting of the Int'l Federation of Foot and Ankle Societies, 1pg, Sep. 2005.

Tasto et al., "Radiofrequency-Based Micro-Tenotomy for Treating Chronic Tendinosis", San Diego Sports Med. and Orthopaedic Ctr, Univ. of California San Diego—Dept. of Orthopaedics, pp. 1-8, 2003.

Tasto, "The Use of Bipolar Radiofrequency Microtenotomy in the Treatment of Chronic Tendinosis of the Foot and Ankle", Techniques in Foot and Ankle Surgery, vol. 5, Issue 2, pp. 110-116, 2006.

Taverna et al., "Arthroscopic Subacromial Decompression versus Radiofrequency (RF) Treatment for Rotator Cuff Tendinopathy A Study of Refractive Superaspinatus Tendinosis", Istituto Ortopedico Galeazzi, Univ. of Milan (Italy), and Dept. of Orthopedics, Univ. of California San Diego, 2pgs, 2005.

Taverna et al., "Radiofrequency-Based Plasma Microtenotomy Compared with Arthoscopic Subacromial Decompression Yields Equivalent Outcomes for Rotator Cuff Tendinosis", The Journal of Arthroscopic and Related Surgery, vol. 23, No. 10, pp. 1042-1051, Oct. 2007.

Weil, Jr. et al., "A New Minimally Invasive Technique for Treating Plantar Fasciosis Using Bipolar Radiofrequency: A Prospective Analysis", Foot & Ankle Specialist, vol. 1, No. 1, pp. 13-18, Feb. 2008.

Weil, Sr. et al., "The Use of Percutaneous Topaz® Coblation for Plantar Fasciosis and Achilles Tendinosis", Weil Foot & Ankle Institute, 1pg, 2007.

Werber et al., "Plasma-Mediated Radiofrequency-Based Microtenotomy for Chronic Tendon Pathology in the Foot", Presented at ACFAS in Las Vegas, NV, 1pg, Mar. 2006.

Wrotslavsky et al., "A Novel Application of Bipolar Radiofrequency in Small Ankle Joints for Arthroscopic Synovectomy", N. General Hospital/N.Y. College of Podiatric Med., New York, Presented as a poster at the ACFAS annual meeting in Las Vegas, NV, 1pg, Mar. 20-21, 2006.

Zang, "Plantar Fasciosis Syndrome: A Retrospective Report on the Endoscopic Micro-Fasciotomy Technique, a Fascia Preservation Procedure", Presented as a poster at the ACFAS annual meeting in Las Vegas, NV, 1pg, Mar. 20-21, 2006.

Zang, "Plantar Plate Derangement with Synovitis of the Second Metatarsal Phalangeal Joint Complex: An Alternative Less Invasive Approach to Surgical Dissection", Presented as a poster at the ACFAS annual meeting in Las Vegas, NV, 1pg, Mar. 20-21, 2006.

* cited by examiner

ELECTROSURGICAL METHOD AND SYSTEM FOR TREATING FOOT ULCER

FIELD OF INVENTION

This invention pertains to electrosurgical systems for treating of ulcer, in particular, an electrosurgical method of treating diabetic foot ulcer whereby an active electrode in the presence of plasma is directed to debride tissue, induce blood flow, and leverage the body's cytokine response to promote healing.

BACKGROUND AND PRIOR ART

An ulcer is a break in a skin or a mucus membrane evident by a loss of surface tissue, tissue disintegration, necrosis of epithelial tissue, nerve damage and pus. On patients with long-standing diabetes and with poor glycemic control, a common condition is diabetic foot ulcer, symptoms of which include surface lesions with peripheral neuropathy, arterial insufficiency, and ischemia of surrounding tissue, deformities, cellulitis tissue formation and inflammation. Cellulitis tissue includes callous and fibrotic tissue. If left untreated a diabetic foot ulcer can become infected and gangrenous which can result in disfiguring scars, foot deformity, and/or amputation.

As illustrated in FIG. 1A, a diabetic foot ulcer may develop on areas of the foot subjected to pressure or injury such as on the dorsal portion of the toes, the pad of the foot, and the heel. Depending on its severity, the condition can vary in size, as illustrated in FIG. 1B, from a small inflammation on the toe with cellulitis and unhealthy tissue that extends up to about 10 mm from the center of the inflammation, to a larger neuropathic lesion on the ball of the foot characterized by cellulitis and unhealthy tissue that extends beyond 2 cm of the perimeter of the perimeter. If the ulcer is accompanied by asteomeylitis, deep abscess or critical ischema, the condition may trigger amputation.

To assist in procedures for treating diabetic foot ulcers, one of several available grading systems such as the Wagner Ulcer Classification System shown in Table 1, below, is used to assess the severity of the ulcer and prescribe treatment. In making the assessment, the ulcer is examined to establish its location, size, depth, and appearance to determine whether it is neuropathic, ischemic, or neuro-ischemic. Depending on the diagnosis, an antibiotic is administered and if further treatment is necessary, the symptomatic area is treated more aggressively, for example, by debridement of unhealthy tissue to induce blood flow and to expose healthy underlying tendons and bone. If warranted, post-debridement treatment such as dressings, foams, hydrocolloids, genetically engineered platelet-derived growth factor becaplermin and bio-engineered skins and the like are applied.

TABLE 1

Wagner Ulcer Classification System

| Grade Classification | Type of Lesion |
|---|---|
| 0 | No open lesion (may have some cellulitis) |
| 1 | Superficial (partial or full thickness cellulitis) |
| 2 | Ulcer extension to ligament, tendon, joint capsule without abscess or osteomyelitis |
| 3 | Deep ulcer with abscess, osteomyelitis, or joint sepsis |
| 4 | Gangrene localized to portion of forefoot or heel |
| 5 | Extensive gangrenous involvement of the entire foot |

In treating ulcers including diabetic foot ulcers, it has been recognized that early intervention to treat affected tissue before a lesion breaks out is beneficial, particularly to debride tissue, increase blood flow and stimulate healthy tissue growth. Topical debriding enzymes are sometime used but are expensive and have not been conclusively shown to be beneficial. After the condition has progressed to a lesion with extensive cellulitis, later stage intervention is also beneficial if the treatment involves removal of unhealthy tissue, increasing blood flow, and stimulating healthy tissue growth. It is therefore an objective to provide methods and systems to facilitate these goals.

SUMMARY OF THE INVENTION

In one embodiment, the method is an electrosurgical procedure for treating ulcer, in particular diabetic foot ulcer, comprising: positioning an active electrode in close proximity to the ulcer, the active electrode disposed on a distal end of an electrosurgical probe or shaft; and applying a high-frequency voltage potential difference across the active electrode and a return electrode sufficient to generate plasma at the active electrode, and to modify the ulcer. In one embodiment, an electrically conductive fluid is provided at the active electrode. Modification of the ulcer in accordance with the present method include perforating tissue in the vicinity of the ulcer, debriding tissue to increase blood flow, and applying plasma to leverage the body's natural healing response. In one embodiment, current is conducted into the ulcer to perforate and remove unhealthy tissue, restore blood flow and promote healing.

In using plasma to modify ulcer, the present method removes unhealthy tissue and improve blood flow, and also leverages the body's cytokine role in coordinating inflammatory response and repairing tissue as described in "*Percutaneous Plasma Discetomy Stimulates Repair In Injured Intervertebral Discs*", Conor W. O'Neill, et al., Department of Orthopedic Surgery, Department of Radiology, University of California, San Francisco, Calif. (2004) herein incorporated by reference.

As noted in the O'Neil reference, plasma alters the expression of inflammatory response in tissue, leading to a decrease in interlukin-1 (IL-1) and an increase in interlukin-8 (IL-8). While both IL-1 and IL-8 have hyperalgesic properties, IL-1 is likely to be the more important pathophysiologic factor in pain disorders than IL-8. Also, as described in the O'Neil reference, cytokines play an important role in coordinating inflammatory and repair response to tissue injury. For example, IL-1 is a catabolic mediator that induces proteases and inhibits extra-cellular matrix synthesis. On the other hand, IL-8 is anabolic as it promotes a number of tissue repair functions including angiogenesis, fibroblast proliferation and differentiation, stem cell mobilization, and maturation and remodeling of matrix. Thus a decrease in IL-1 and an increase in IL-8 suggest that plasma has a role in stimulating a healing response mediated by IL-8 to mediate tissue degeneration, resulting in overall tissue healing, an a decrease in inflammation and pain.

Since the method can be applied at any stage of the condition, the method can therefore be used to treat ulcerated tissue both before and after a lesion forms. Hence, both the early stages of the condition before extensive tissue damage have occurred, and at a later stage when there is extensive tissue damage and cellulitis can be treated.

Embodiments of the present methods and system are described and illustrated in the following detailed specification.

DETAILED DESCRIPTION

Figure 1A:
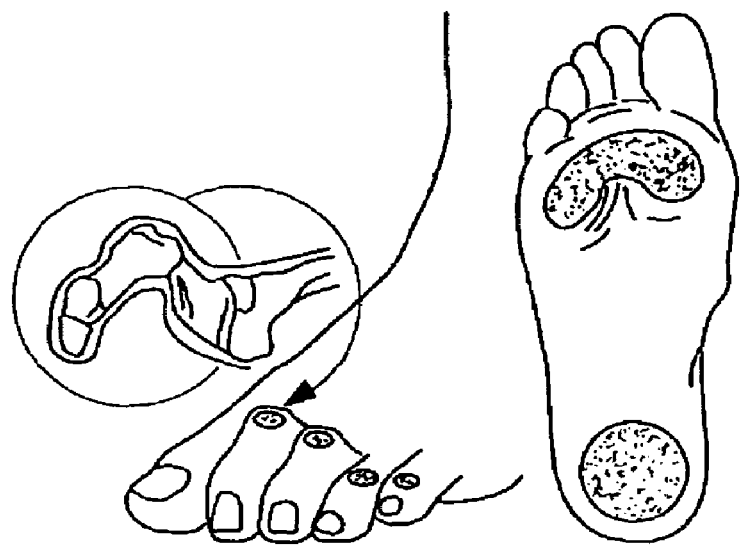
FIG. 1A is an illustration of ulcer locations on a foot.
Figure 1B:
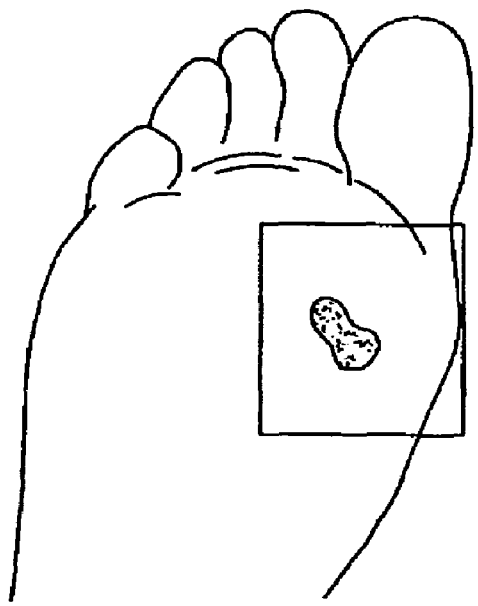
FIG. 1B is an illustration of a diabetic foot ulcer on the pad of the foot.

Electrosurgical apparatus and systems adaptable for use with the present method are illustrated and described in commonly owned U.S. Pat. Nos. 6,296,638, 6,602,248 and 6,805,130 the disclosure of which is herein incorporated by reference. In one exemplary embodiment illustrated in FIG. 2, the electrosurgical system (8) includes a probe (10) comprising an elongated shaft (12) and a connector (14) at its proximal end, and one or more active electrodes (16A) disposed on the distal end of the shaft. Also disposed on the shaft but spaced from the active electrode is a return electrode (16B). A handle (20) with connecting power cable (18) and cable connector (22) can be removably connected to the power supply (26).

As used herein, an active electrode is an electrode that is adapted to generate a higher charge density, and hence generate more plasma, relative to a return electrode when a high-frequency voltage potential is applied across the electrodes, as described herein. Typically, a higher charge density is obtained by making the active electrode surface area smaller relative to the surface area of the return electrode.

Power supply (26) comprises selection means (28) to change the applied voltage level. The power supply (26) can also include a foot pedal (32) positioned close to the user for energizing the electrodes (16A, 16 B). The foot pedal (32) may also include a second pedal (not shown) for remotely adjusting the voltage level applied to electrodes (16A, 16B). Also included in the system is an electrically conductive fluid supply (36) with tubing (34) for supplying the probe (10) and the electrodes with electrically conductive fluid. Details of a power supply that may be used with the electrosurgical probe of the present invention is described in commonly owned U.S. Pat. No. 5,697,909 which is hereby incorporated by reference herein.

Figure 2:
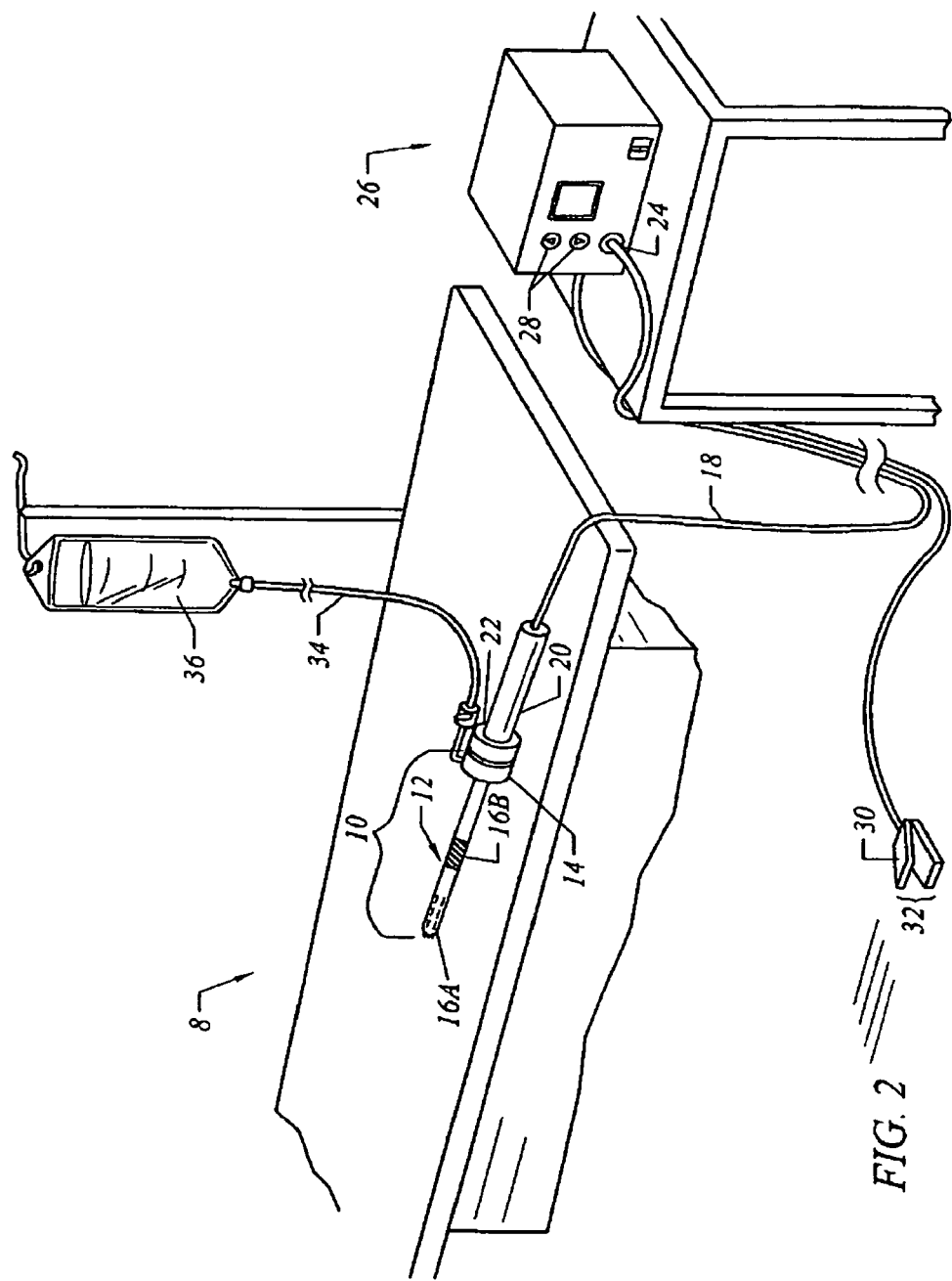
FIG. 2 is an illustration of an electrosurgical system adaptable for use with the present method.

As illustrated in FIG. 2, the return electrode (16B) is connected to power supply (26) via cable connectors (18), to a point slightly proximal of active electrode. Typically the return electrode is spaced at about 0.5 mm to 10 mm, and more preferably about 1 mm to 10 mm from the active electrode. Shaft (12) is disposed within an electrically insulative jacket, which is typically formed as one or more electrically insulative sheaths or coatings, such as polyester, polytetrafluoroethylene, polyimide, and the like. The provision of the electrically insulative jacket over shaft (12) prevents direct electrical contact between shaft (12) and any adjacent body structure or the surgeon. Such direct electrical contact between a body structure and an exposed return electrode (16B) could result in unwanted heating of the structure at the point of contact causing necrosis.

As will be appreciated, the above-described systems and apparatus can applied equally well to a wide range of electrosurgical procedures including open procedures, intravascular procedures, urological, laparoscopic, arthroscopic, thoracoscopic or other cardiac procedures, as well as dermatological, orthopedic, gynecological, otorhinolaryngological, spinal, and neurologic procedures, oncology and the like. However, for the present purposes the system described herein is directed to treat various forms of ulcer, including skin ulcer, mucus membrane ulcer, foot ulcer, cellulitic tissue, and diabetic foot ulcer.

In accordance with the present method, the system of FIG. 2 is adaptable to apply a high frequency (RF) voltage/current to the active electrode(s) in the presence of electrically conductive fluid to modify the structure of tissue on and in the vicinity of the ulcer. Thus, with the present method, the system of FIG. 2 can be used to modify tissue by: (1) creating perforations in the vicinity of the ulcer; (2) volumetrically removing tissue, including bone and cartilage in the vicinity of the ulcer (i.e., ablate or effect molecular dissociation of the tissue structure) from on and around the ulcer; (3) forming holes, channels, divots, or other spaces on the ulcer; (4) cutting or resect tissues of the ulcer; (5) shrinking or contracting collagen-containing connective tissue in and around the ulcer and/or (6) coagulate severed blood vessels in and around the ulcer.

In accordance with the present method, the applied current can be used to modify tissue in several ways, e.g., the current can be passed directly into the target site by direct contact with the electrodes such to heat the target site; or the current can be passed indirectly into the target site through an electrically conductive fluid located between the electrode and the target site also to heat the target site; or current can be passed into an electrically conductive fluid disposed between the electrodes to generate plasma for treating the target site. In accordance with the present method, the high frequency voltage difference applied between one or more active electrode(s) and one or more return electrode(s) develop high electric field intensities in the vicinity of the target tissue. The high electric field intensities adjacent to the active electrode(s) induces molecular breakdown of target tissue by molecular dissociation of tissue components (rather than by thermal evaporation or carbonization). In this procedure it is believed that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of water from within the cells of the tissue.

The high electric field intensities is generated, in accordance with the present method, by applying a high frequency voltage that sufficient to vaporize electrically conductive fluid disposed over at least a portion of the active electrode(s) in the region between the distal tip of the active electrode(s) and the target tissue. The electrically conductive fluid may be a liquid, such as isotonic saline, Ringer's lactate solution, blood and other body fluids delivered to the target site, or a viscous fluid, such as a conductive gel, applied to the target site. Since the vapor layer or vaporized region has relatively high electrical impedance, it minimizes current flow into the electrically conductive fluid. This ionization, under these conditions, induces the discharge of plasma comprised of energetic electrons and photons from the vapor layer and to the surface of the target tissue. A more detailed description of this phenomenon, termed Coblation™, can be found in commonly assigned U.S. Pat. No. 5,683,366 the complete disclosure of which is incorporated herein by reference.

In various embodiments of the present method, the electrically conductive fluid possesses an electrical conductivity value above a minimum threshold level, in order to provide a suitable conductive path between the return electrode and the active electrode(s). The electrical conductivity of the fluid (in units of milliSiemens per centimeter or mS/cm) is usually be greater than about 0.2 mS/cm, typically greater than about 2 mS/cm and more typically greater than about 10 mS/cm. In an exemplary embodiment, the electrically conductive fluid is isotonic saline, which has a conductivity of about 17 mS/cm.

Also in various embodiments of the preset method, it may be necessary to remove, e.g., aspirate, any excess electrically conductive fluid and/or ablation by-products from the surgical site. In addition, it may be desirable to aspirate small pieces of tissue that are not completely disintegrated by the high frequency energy, or other fluids at the target site, such as blood, mucus, and other body fluids.

Accordingly, in various embodiments the present system includes one or more suction lumen(s) in the shaft, or on another instrument, coupled to a suitable vacuum source for aspirating fluids from the target site. In various embodiments, the instrument also includes one or more aspiration electrode(s) coupled to the aspiration lumen for inhibiting clogging during aspiration of tissue fragments from the surgical site. A more complete description of these embodiments can be found in commonly owned U.S. Pat. No. 6,190,381, the complete disclosure of which is incorporated herein by reference for all purposes.

In the present method a single electrode or an electrode array may be disposed over a distal end of the shaft of the electrosurgical instrument to generate and apply the plasma to the tissue. In both configurations, the circumscribed area of the electrode or electrode array will generally depend on the desired diameter of the perforations and amount of debriding to be performed. In one embodiment, the area of the electrode array is in the range of from about 0.25 mm$^2$ to 20 mm$^2$, preferably from about 0.5 mm$^2$ to 10 mm$^2$, and more preferably from about 0.5 mm$^2$ to 5.0 mm$^2$.

In addition, the shape of the electrode at the distal end of the instrument shaft will also depend on the size of the surface area to be treated. For example, the electrode may take the form of a pointed tip, a solid round wire, or a wire having other solid cross-sectional shapes such as squares, rectangles, hexagons, triangles, star-shaped, or the like, to provide a plurality of edges around the distal perimeter of the electrodes. Alternatively, the electrode may be in the form of a hollow metal tube having a cross-sectional shape that is round, square, hexagonal, rectangular or the like. The envelope or effective diameter of the individual electrode(s) ranges from about 0.05 mm to 3 mm, preferably from about 0.1 mm to 2 mm.

Figure 3A:
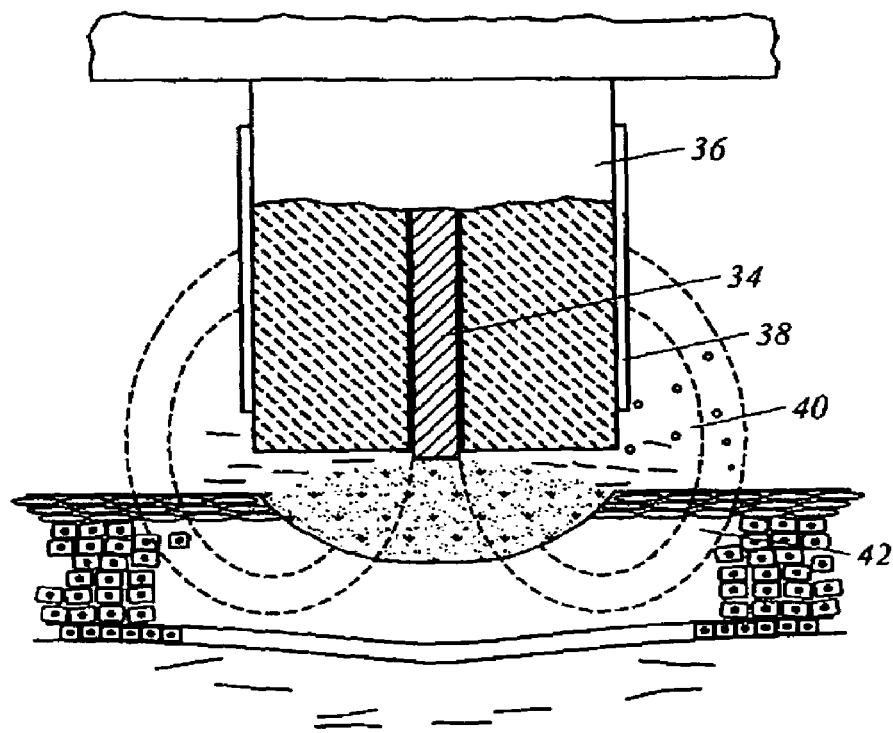
FIG. 3A is an illustration of an electrode configuration for debriding ulcerated tissue in accordance with the present method.
Figure 3B:
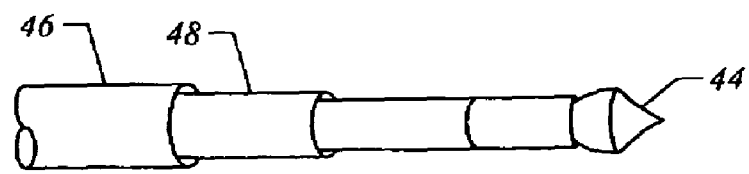
FIG. 3B is an illustration of an electrode configuration for perforating ulcerated tissue in accordance with the present method.

Examples of an electrosurgical apparatus that can be used to modify tissue in accordance with the present method are illustrated in FIGS. 3A and 3B. With reference to FIG. 3A, in one embodiment the apparatus comprises an active electrode (34) disposed on the distal end of a shaft (36). Spaced from the active electrode is a return electrode (38) also disposed on the shaft. Both the active and return electrodes are connected to a high frequency voltage supply (not shown). Disposed in contact with the active and return electrodes is an electrically conductive fluid (40). In one embodiment the electrically conductive fluid forms an electrically conductive fluid bridge (42) between the electrodes. On application of a high frequency voltage across the electrode, plasma is generated as described above, for use in treating tissue in accordance with the present method. A more detailed description of this phenomenon, termed Coblation™, and the operation of the electrode illustrated in FIG. 3A can be found in commonly assigned U.S. Pat. No. 6,296,638 the complete disclosure of which is incorporated herein by reference. Advantageously, as the tip of the electrode (34) presents a relatively broad surface area, the electrode tip illustrated in FIG. 3A is beneficially used for treating larger ulcers including debriding large amounts of dead or necrotic tissue, in accordance with the present method.

Similarly, with reference to FIG. 3B, in one embodiment the apparatus comprises an active electrode (44) disposed on the distal end of a shaft (46) Spaced from the active electrode is a return electrode (48) also disposed on the shaft. Both the active and return electrodes are connected to a high frequency voltage supply (not shown). On application of a high frequency voltage across the electrode in the presence of a conductive fluid plasma id generated for use in treating tissue in accordance with the present method. A more detailed description of this phenomenon, termed Coblation™, and the operation of the electrode illustrated in FIG. 3B can be found in commonly assigned U.S. Pat. No. 6,602,248 the complete disclosure of which is incorporated herein by reference. Advantageously, as the tip of the electrode (34) presents a pointed, the electrode tip of FIG. 3B is beneficially used for perforating smaller areas of tissue in the vicinity of the ulcer to induce blood flow to the tissue.

In a typical procedure involving treatment of diabetic foot ulcer, it may be necessary to use one or more shapes of electrodes. For example, in a first step, an electrode of the type illustrated in FIG. 3A may be employed to debride large area of unhealthy tissue surrounding the ulcer. Thereafter, an electrode as shown in FIG. 3B can be used to perforate the debrided area to induce blood flow.

The area of the tissue treatment surface can vary widely, and the tissue treatment surface can assume a variety of geometries, with particular areas and geometries being selected for specific applications. The active electrode surface(s) can have area(s) in the range from about 0.25 mm$^2$ to 75 mm$^2$, usually being from about 0.5 mm$^2$ to 40 mm$^2$. The geometries can be planar, concave, convex, hemispherical, conical, linear "in-line" array, or virtually any other regular or irregular shape.

Most commonly, the active electrode(s) or active electrode array(s) will be formed at the distal tip of the electrosurgical instrument shaft, frequently being planar, disk-shaped, pointed or hemispherical surfaces for use in reshaping procedures, or being linear arrays for use in cutting. Alternatively or additionally, the active electrode(s) may be formed on lateral surfaces of the electrosurgical instrument shaft (e.g., in the manner of a spatula).

The voltage difference applied between the return electrode(s) and the return electrode is high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (e.g., contraction, coagulation, cutting or ablation).

Typically, the peak-to-peak voltage for ablation or cutting of tissue will be in the range of from about 10 volts to 2000 volts, usually in the range of 200 volts to 1800 volts, and more typically in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably from about 100 to 1000, and more preferably from about 120 to 600 volts peak-to-peak The power source may be current limited or otherwise controlled so that undesired heating of the target tissue or surrounding (non-target) tissue does not occur. In a preferred embodiments, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. A more detailed description of this phenomenon, termed Coblation™, can be found in commonly assigned U.S. Pat. No. 5,683,366 the complete disclosure of which is incorporated herein by reference.

The current flow path between the active electrodes and the return electrode(s) may be generated by submerging the tissue site in an electrically conductive fluid (e.g., a viscous fluid, such as an electrically conductive gel), or by directing an electrically conductive fluid through a fluid outlet along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., as compared with containment of a liquid, such as isotonic saline). A more complete description of an exemplary method of directing electrically conductive fluid between active and return electrodes is described in U.S. Pat. No. 5,697,281, the contents of which are incorporated by reference herein in their entirety.

Figure 4:
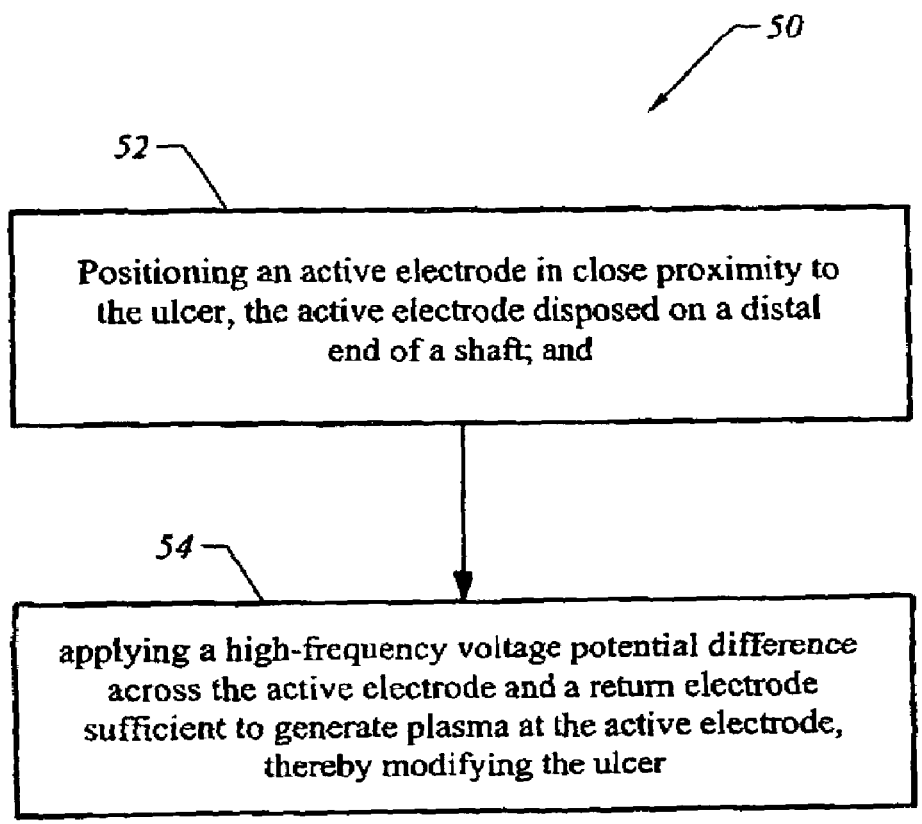
FIG. 4 is an algorithm of an embodiment of the present method.

With reference to FIG. 4, the present method in one embodiment is a procedure for treating ulcers, including skin ulcer, mucus membrane ulcers, foot ulcers, a diabetic foot ulcer to promote healing. In particular embodiments, the method (50) includes the steps of: (52) positioning an active electrode in close proximity to the ulcer, the active electrode disposed on a distal end of a shaft; and (54) applying a high-frequency voltage potential difference across the active electrode and a return electrode sufficient to generate plasma at the active electrode, whereby the ulcer is modified by the active electrode.

In one embodiment, a conductive fluid such as isotonic saline, a conductive gel, Ringer's solution and body fluid such as blood and body plasma is preset and is in contact with the active electrode. As noted above, the conductive fluid in the presence of a sufficiently high-frequency voltage will generate plasma as used in the present method.

In one embodiment, the conductive fluid forms a conductive bridge between the active electrode and the return electrode. In this embodiment, the active and return electrodes are disposed on the distal end of an electrosurgical shaft as described above. Thus in this embodiment, since current does not pass into the tissue, plasma generated in the conductive fluid is used to modify the tissue as described above.

In an alternative embodiment, an electrically conductive fluid layer is provided in between the active electrode and the tissue, in the vicinity of the tissue. In this embodiment, in addition to plasma generated in the fluid, current from the applied high frequency voltage is applied into the tissue. Thus with this embodiment, both current and plasma are used to modify the tissue. In one embodiment the applied high frequency voltage is adjusted to provide sufficient current for coagulating and sealing the tissue and stop bleeding.

In various embodiments of the method, a suitably configured active electrode is used to treat the ulcer, for example, by debriding, perforating, inducing blood-flow to tissue, coagulating tissue and volumetrically removing tissue in the vicinity of the ulcer. Thus, for example, an active electrode as schematically illustrated in FIG. 3A and comprised of a relatively wide distal end can be used to debride and volumetrically remove unhealthy tissue in the vicinity of the ulcer. Thereafter, in accordance with the present method, the smaller active electrode schematically illustrated in FIG. 3B can be used to perforate the tissue in the debrided area to cause blood flow for healing.

In use, the active electrode is translated axially and radially over the tissue in the proximity of the ulcer to modify the tissue. Depending on the size of the debrided area and the lesion, small wounds can be treated by a needle-type active electrode as illustrated in FIG. 3B wherein many perforations are applied on the ulcer in an random manner, whereas for cellulitis in the vicinity of the ulcer, the perforations may be applied in an grid-like manner. For larger and more complicated ulcers, an electrode with a wider tip as illustrated in FIG. 3A can be used for more aggressive treatment.

In various embodiments, the tissue in the vicinity of the ulcer is treated with the active electrode for about 0.5 seconds at a time. Depending on the size of the area to be treated the method in one embodiment involves perforating the tissue at about 2 to 5 mm apart in the vicinity of the ulcer to form perforations with diameters of up to about 3 mm, and about 3 mm to 5 mm in depth.

In both types of electrode configurations, an electrically conductive fluid is provided to generate plasma. Depending on the apparatus used, the conductive fluid is provide by a lumen that discharges the fluid in the vicinity of the tissue. Similarly, in alternate embodiments, a suction lumen is provided to suction fluid and body tissue from the vicinity of the ulcer.

While the invention is described with reference to the Figures and method herein, it will be appreciate by one ordinarily skilled in the art that the invention can also be practiced with modifications within the scope of the claims. The scope of the invention therefore should not be limited to the embodiments as described herein, but is limited only by the scope of the appended claims.

The invention claimed is:

1. An electrosurgical method of treating ulcer tissue to promote healing, comprising:
    positioning an active electrode in close proximity to the ulcer tissue, the active electrode disposed on a distal end of a shaft; and
    applying a high-frequency voltage potential difference across the active electrode and a return electrode sufficient to generate plasma at the active electrode,
    whereby the active electrode modifies the ulcer tissue, and wherein modifying the ulcer tissue comprises debriding, perforating, inducing blood-flow to, coagulating, and volumetrically removing ulcer tissue.

2. The method of claim 1, wherein an electrically conductive fluid is provided on the active electrode.

3. The method of claim 1, wherein the ulcer tissue comprises a skin ulcer.

4. The method of claim 1, whereby modifying the ulcer tissue comprises directing plasma to the ulcer tissue.

5. The method of claim 1, wherein modifying the ulcer tissue comprises passing an electric current through the ulcer tissue.

6. The method of claim 1, whereby positioning the active electrode comprises translating the active electrode axially and radially over tissue in the proximity of the ulcer tissue.

7. The method of claim 1, wherein the active and the return electrode are disposed on the shaft.

8. The method of claim 1, wherein the return electrode is prevented from contacting tissue in the vicinity of the ulcer tissue.

9. The method of claim 2, wherein the electrically conductive fluid comprises a conductive layer disposed on the active electrode.

10. The method of claim 2, where plasma is generated from the electrically conductive fluid.

11. The method of claim 2, wherein the electrically conductive fluid comprises a conductive bridge disposed between the active and return electrodes.

12. The method of claim 2, wherein the electrically conductive fluid comprises, body fluid, a conductive gel, isotonic saline and Ringer's lactate solution.

13. The method of claim 1, including contacting the ulcer tissue with the active electrode.

14. The method of claim 1, including flooding the ulcer tissue with conductive fluid.

15. The method of claim 1, including directing plasma intermittingly to contact tissue in the vicinity of the ulcer tissue for about 0.5 seconds on each instance.

16. The method of claim 1, wherein perforating the tissue comprises forming perforations at about 2 to 5 mm apart in the ulcer tissue and in the vicinity of the ulcer tissue.

17. The method of claim 1, wherein perforating the tissue comprises forming perforations with diameters of up to about 3 mm in the ulcer tissue and in the vicinity of the ulcer tissue.

18. The method of claim 1, wherein perforating the tissue comprises forming perforations up to about 3 mm deep in the ulcer tissue and in the vicinity of the ulcer tissue.

19. The method of claim 1, wherein perforating the tissue comprises forming perforations up to about 5 mm deep in the ulcer tissue and in the vicinity of the ulcer tissue.

20. The method of claim 1, including adjusting the voltage to cause coagulation of tissue in the vicinity of the ulcer tissue.

21. The method of claim 1, wherein the active electrode is attached to a voltage regulator and a conductive fluid supply.

22. The method of claim 1, wherein the active electrode is selected from the group consisting of an electrode having a pointed tip, a wire electrode, a screen electrode, and a suction electrode.

23. The method of claim 1, wherein the shaft comprises a suction lumen adapted for suctioning tissue from the vicinity of the ulcer tissue.

24. The method of claim 1, wherein the shaft comprises a fluid discharge lumen adapted for delivering conductive fluid in the vicinity of the active electrode.

25. The method of claim 1, wherein the ulcer tissue comprises a mucus membrane ulcer.

26. The method of claim 1, wherein the ulcer tissue comprises a foot ulcer.

27. The method of claim 1, wherein the ulcer tissue comprises a diabetic foot ulcer.

28. The method of claim 1, wherein the ulcer tissue comprises cellulitic tissue.

29. The method of claim 1, wherein modifying the ulcer tissue further comprises debriding, perforating, inducing blood-flow to, coagulating, and volumetrically removing tissue in the vicinity of the ulcer tissue.

* * * * *